US012763171B2

(12) United States Patent
Takahashi

(10) Patent No.: US 12,763,171 B2
(45) Date of Patent: Oct. 13, 2026

(54) STORAGE MEDIUM, QUANTUM CHEMICAL COMPUTING METHOD, AND QUANTUM CHEMICAL COMPUTING DEVICE

(71) Applicant: FUJITSU LIMITED, Kawasaki (JP)

(72) Inventor: Norihiko Takahashi, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 774 days.

(21) Appl. No.: 18/301,289

(22) Filed: Apr. 17, 2023

(65) Prior Publication Data

US 2024/0013865 A1 Jan. 11, 2024

Related U.S. Application Data

(63) Continuation of application No. PCT/JP2020/041725, filed on Nov. 9, 2020.

(51) Int. Cl.

*G16C 10/00* (2019.01)
*G06N 10/20* (2022.01)
*G06N 10/40* (2022.01)

(52) U.S. Cl.

CPC ............. *G16C 10/00* (2019.02); *G06N 10/40* (2022.01)

(58) Field of Classification Search

CPC ......... G16C 10/00; G06N 10/40; G06N 10/20
See application file for complete search history.

(56) References Cited

U.S. PATENT DOCUMENTS 10,592,815 B2 * 3/2020 Yoshida ................. B82Y 10/00
2008/0059549 A1 3/2008 Aoki et al.
2016/0371467 A1 12/2016 Lee et al.
2018/0268316 A1 9/2018 Yoshida
2020/0294630 A1 * 9/2020 Miller .................... G16C 20/10
(Continued)

FOREIGN PATENT DOCUMENTS

JP H10-83389 A 3/1998
JP 2005-202855 A 7/2005
JP 2005-242563 A 9/2005
(Continued)

OTHER PUBLICATIONS

Extended European Search Report dated Nov. 21, 2023 for corresponding European Patent Application No. 20960850.4, 7 pages.
(Continued)

*Primary Examiner* — Nghia M Doan

(74) *Attorney, Agent, or Firm* — Fujitsu Intellectual Property Center

(57) ABSTRACT

A non-transitory computer-readable storage medium storing a quantum chemical computing program that causes at least one computer to execute a process, the process includes generating a plurality of molecular orbital pairs that indicates a plurality of patterns of combination of two molecular orbitals, based on a plurality of molecular orbitals for a molecule subject to quantum chemical computations; computing, for each of the plurality of molecular orbital pairs, an overlap integral value between included molecular orbitals; and determining first molecular orbitals to be included in an active space orbital group in the quantum chemical computations, based on the overlap integral value of each of the plurality of molecular orbital pairs.

10 Claims, 10 Drawing Sheets

(56) References Cited

U.S. PATENT DOCUMENTS

2022/0019931 A1 * 1/2022 Jiang ........................ G06F 9/455

FOREIGN PATENT DOCUMENTS

| | | |
|---|---|---|
| JP | 2006-092421 A | 4/2006 |
| JP | 2008-009706 A | 1/2008 |
| JP | 2018-152018 A | 9/2018 |

OTHER PUBLICATIONS

Stein, Christopher J. et al., "Automated Selection of Active Orbital Spaces", ARXIV, Feb. 11, 2016, pp. 1-29, XP080798190, DOI: 10.1021/ACS.JCTC.6B00156.

Veryazov, Valera et al., "How to Select Active Space for Multiconfigurational Quantum Chemistry?", International Journal of Quantum Chemistry, vol. 111, No. 13, Apr. 25, 2011, pp. 3329-3338, XP071305265.

Chinese Office Action issued Aug. 24, 2024 for corresponding Chinese Patent Application No. 202080106749.8, 15 pages.

Takeshi Yanai et al., "Computational Science of Molecuar Systems: Dynamics and Structure of Many-electron and Many-atom Systems", Computational Science and Engineering, Kyoritsu Shuppan Co., Ltd., 1st Edition, vol. 6, ISBN: 978-4-320-12271-0, pp. 78-80, Nov. 30, 2010 (Total 6 pages) (Cited in ISR).

International Search Report and Written Opinion of the International Searching Authority (Form PCT/ISA/210, 220, and 237), mailed in connection with PCT/JP2020/041725 and mailed Feb. 2, 2021 (Total 11 pages).

* cited by examiner

FIG. 7

111 method: Hartree-Fock
basis: STO-3G
charge: 0
spin multiplicity: 1
geometry: [["Li", [0, 0, 0]], ["H", [0, 0, 1.4]]]
energy level minimum: -2.0
energy level maximum: 1.0

STORAGE MEDIUM, QUANTUM CHEMICAL COMPUTING METHOD, AND QUANTUM CHEMICAL COMPUTING DEVICE

CROSS-REFERENCE TO RELATED APPLICATION

This application is a continuation application of International Application PCT/JP2020/041725 filed on Nov. 9, 2020 and designated the U.S., the entire contents of which are incorporated herein by reference.

FIELD

The present invention relates to a storage medium, a quantum chemical computing method, and a quantum chemical computing device.

BACKGROUND

Quantum chemical computations can be performed using classical computers or quantum computers. Quantum chemical computations precisely solve the Schrödinger equation, which deals with atomic nuclei and electrons.

In quantum chemical computations, in order to incorporate the effect of electron correlation and perform highly accurate computations, for example, the configuration interaction method (CI method) is used, which solves the wave function by taking a plurality of electron configurations into consideration. In the CI method, for example, computations are performed taking into consideration a plurality of electron configurations created using molecular orbitals obtained by the Hartree-Fock method.

As a technique related to quantum chemical computations, for example, a quantitative analysis system for quantitatively analyzing molecular orbital distribution has been proposed. In addition, a computing device that suppresses the amount of computation when computing the all-electron wave function has also been proposed.

Patent Document 1: U.S. Patent Application Publication No. 2016/0371467, Patent Document 2: Japanese Laid-open Patent Publication No. 2018-152018.

SUMMARY

According to an aspect of the embodiments, a non-transitory computer-readable storage medium storing a quantum chemical computing program that causes at least one computer to execute a process, the process includes generating a plurality of molecular orbital pairs that indicates a plurality of patterns of combination of two molecular orbitals, based on a plurality of molecular orbitals for a molecule subject to quantum chemical computations; computing, for each of the plurality of molecular orbital pairs, an overlap integral value between included molecular orbitals; and determining first molecular orbitals to be included in an active space orbital group in the quantum chemical computations, based on the overlap integral value of each of the plurality of molecular orbital pairs.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 7 is a diagram illustrating an example of computation condition data;

DESCRIPTION OF EMBODIMENTS

When the scale of the system is small and the number of basis functions is small, the number of molecular orbitals (number of basis functions) obtained by the Hartree-Fock method is also small. Therefore, it is also practicable to perform computations taking all possible electron configurations into consideration (full-CI computations). On the other hand, as the scale of the system increases and the number of basis functions increases, the number of molecular orbitals obtained by the Hartree-Fock method also increases, making the full-CI computations difficult.

When the full-CI computations are difficult, it is effective to choose an electron configuration that contributes as much as possible to the effect of electron correlation and to perform computations taking the chosen electron configuration into consideration. The set of one or more molecular orbitals (molecular orbital group) in which the electrons are placed in the electron configurations taken into consideration at this time is called the active space orbital group. It is important to select an appropriate active space orbital group in order to suppress the computational load and to perform accurate computations that incorporate more effects of electron correlation.

However, traditionally, there has been no criterion for selecting appropriate molecular orbitals to perform accurate computations that incorporate more effects of electron correlation, and it has not been achieved to deter degradation of computation accuracy due to limiting the molecular orbitals to which electrons are placed to the active space orbital group. Therefore, when attempting to carry out quantum chemical computations with high accuracy, there is no option but to perform the full-CI computations, making it difficult to reduce the amount of computation.

In one aspect, an object of the present invention is to reduce the amount of computation of quantum chemical computations.

According to one form, the amount of computation of quantum chemical computations may be reduced.

The above-described object and other objects, features, and advantages of the present invention will become clear from the following description related to the appended drawings, which represent preferred embodiments as examples of the present invention.

Hereinafter, the present embodiments will be described with reference to the drawings. Note that each of the embodiments may be carried out in combination with a plurality of embodiments as long as no contradiction arises.

First Embodiment

First, as a first embodiment, a quantum chemical computing method capable of reducing the amount of computation of quantum chemical computations will be described.

Figure 1:
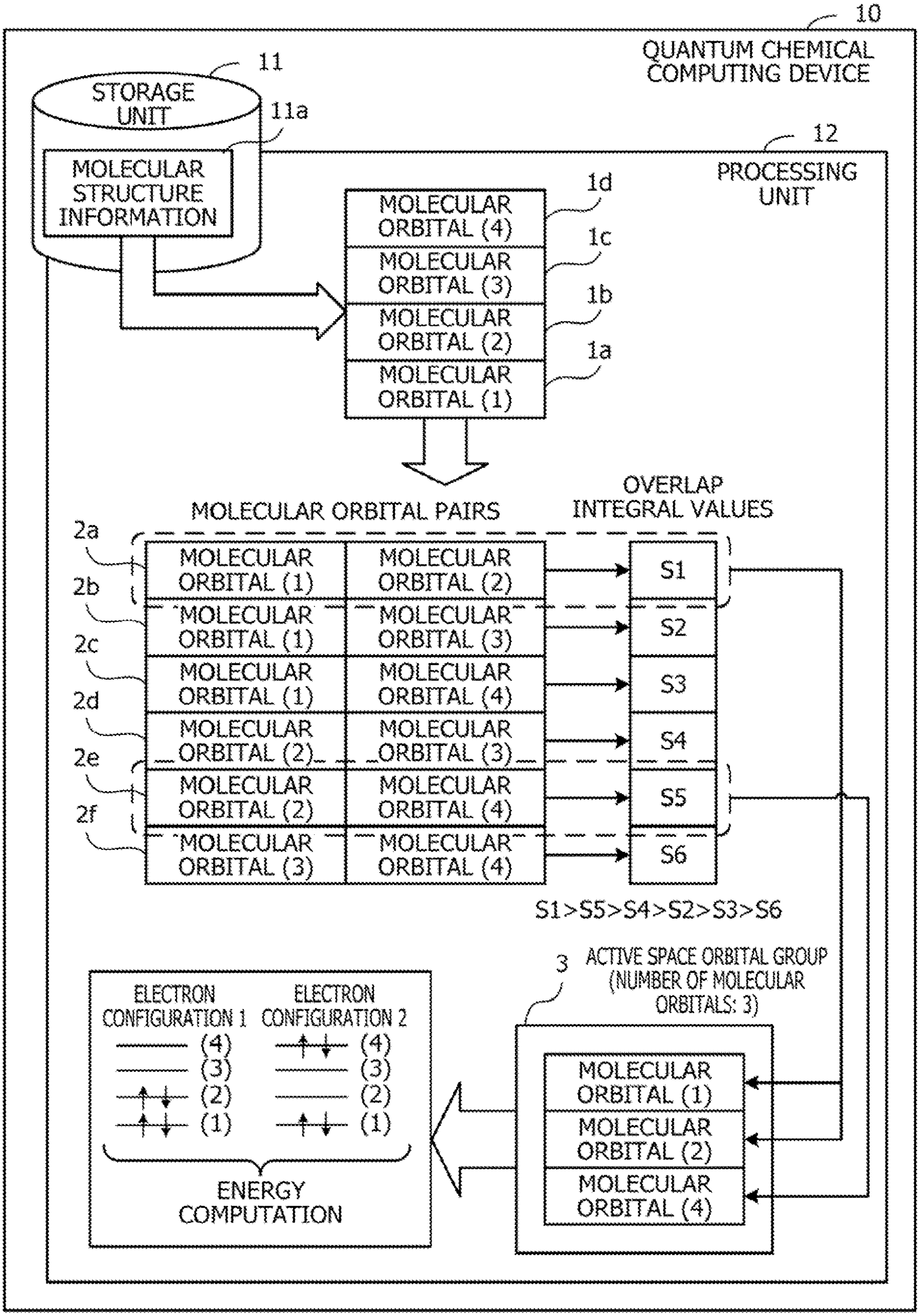
FIG. 1 is a diagram illustrating an example of a quantum chemical computing method according to a first embodiment.

FIG. 1 is a diagram illustrating an example of the quantum chemical computing method according to the first embodiment. FIG. 1 illustrates an example of a case where the quantum chemical computing method capable of reducing the amount of computation is carried out using a quantum chemical computing device 10. The quantum chemical computing device 10 can carry out the quantum chemical computing method by executing a quantum chemical computing program, for example.

The quantum chemical computing device 10 includes a storage unit 11 and a processing unit 12. The storage unit 11 is, for example, a memory or a storage device included in the quantum chemical computing device 10. The processing unit 12 is, for example, a processor or an arithmetic circuit included in the quantum chemical computing device 10.

The storage unit 11 stores, for example, molecular structure information 11*a* on molecules subject to quantum chemical computations. The molecular structure information 11*a* includes information on atoms included in the relevant molecule, bond distances and bond accuracy between atoms, and the like.

The processing unit 12 performs quantum chemical computations based on the molecular structure information 11*a*. For example, the processing unit 12 calculates a plurality of molecular orbitals 1*a* to 1*d* for a molecule subject to quantum chemical computations, based on the molecular structure information 11*a*.

Note that, when the plurality of molecular orbitals 1*a* to 1*d* of the molecule is known, information indicating the plurality of molecular orbitals 1*a* to 1*d* also can be stored in the storage unit 11 in advance. In that case, the processing unit 12 acquires the information indicating the plurality of molecular orbitals 1*a* to 1*d* from the storage unit 11.

Next, the processing unit 12 generates a plurality of molecular orbital pairs 2*a* to 2*f* indicating a plurality of patterns of combination of two molecular orbitals, based on the plurality of molecular orbitals 1*a* to 1*d*. In the example in FIG. 1, six molecular orbital pairs 2*a* to 2*f* are generated based on the four molecular orbitals 1*a* to 1*d*.

The processing unit 12 computes, for each of the plurality of molecular orbital pairs 2*a* to 2*f*, the value of the overlap integral between the included molecular orbitals (overlap integral value). The overlap integral values of the plurality of molecular orbital pairs 2*a* to 2*f* are assumed to be S1 to S6, respectively. At this time, the overlap integral values S1 to S6 are assumed to have a magnitude relationship of S1>S5>S4>S2>S3>S6.

The processing unit 12 determines first molecular orbitals to be included in an active space orbital group 3 in quantum chemical computations, based on the respective overlap integral values S1 to S6 of the plurality of molecular orbital pairs 2*a* to 2*f*. For example, the processing unit 12 determines, as first molecular orbitals, a predetermined number of molecular orbitals in order from the molecular orbital having the largest of the overlap integral values S1 to S6 with other molecular orbitals. The number of molecular orbitals to be included in the active space orbital group 3 is a value smaller than the total number of the plurality of molecular orbitals 1*a* to 1*d*.

When the number of molecular orbitals to be included in the active space orbital group 3 is assumed to be "3", the processing unit 12 first includes the molecular orbitals 1*a* and 1*b* included in the molecular orbital pair 2*a* having the largest overlap integral value, into the active space orbital group 3. Next, the processing unit 12 includes the molecular orbital 1*d*, which is not yet included in the active space orbital group 3 among the molecular orbitals 1*b* and 1*d* included in the molecular orbital pair 2*e* having the second largest overlap integral value, into the active space orbital group 3. Since the number of molecular orbitals of the active space orbital group 3 has now reached "3", the generation of the active space orbital group 3 is completed.

The processing unit 12 computes the molecular energy based on the electron configurations according to the first molecular orbitals included in the active space orbital group 3. For example, the processing unit 12 computes the total energy that integrates the state of each of the plurality of electron configurations indicating a plurality of configuration patterns of the electrons according to the active space orbital group 3. The processing unit 12 outputs the calculated energy value as a result of quantum chemical computations.

According to such a quantum chemical computing device 10, a molecular orbital having a large overlap integral value with another molecular orbital can be included into the active space orbital group 3. The molecular orbital pair having a large overlap integral value also has strong interaction between molecular orbitals. By including molecular orbitals having strong large interaction between the molecular orbitals into the active space orbital group 3, the possibility of creating such an electronic state that lessens the total energy increases, and highly accurate computations may be enabled. In different terms, the full-CI computations are avoided while the computation accuracy is maintained at high accuracy, and a decrease in the amount of computation is achieved.

In addition, the processing unit 12 may combine second molecular orbitals whose energy levels are equal to or higher than a first threshold value but equal to or lower than a second threshold value higher than the first threshold value, from among the plurality of molecular orbitals 1*a* to 1*d*, to generate a plurality of molecular orbital pairs. The molecular orbital whose energy level is lower than the first threshold value is treated as a molecular orbital in which, for example, electrons are regularly placed in energy computations. In addition, the molecular orbital whose energy level is higher than the second threshold value is treated as a molecular orbital in which, for example, electrons are not placed any time in energy computations. In this manner, by limiting the molecular orbitals to be included in the molecular orbital pairs at the stage of generating the molecular orbital pairs, the number of computations of the overlap integral values may be reduced. As a result, processing efficiency may be improved.

Second Embodiment

Next, a second embodiment will be described. In the second embodiment, a computer is caused to execute quantum chemical computations.

Figure 2:
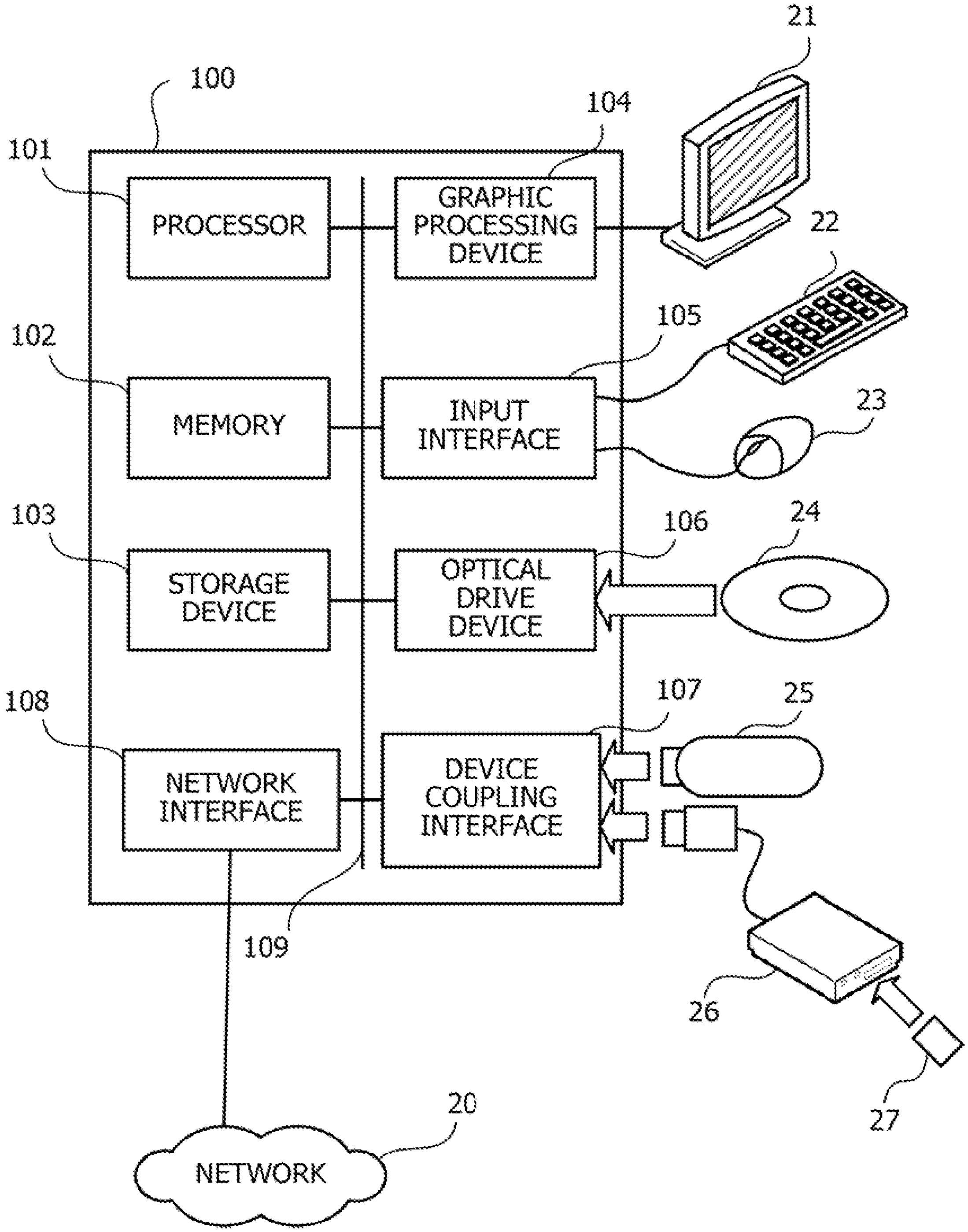
FIG. 2 is a diagram illustrating an example of hardware of a computer used for quantum chemical computations.

FIG. 2 is a diagram illustrating an example of hardware of a computer used for quantum chemical computations. The entire device of a computer 100 is controlled by a processor 101. A memory 102 and a plurality of peripheral devices are coupled to the processor 101 via a bus 109. The processor 101 may be a multiprocessor. The processor 101 is, for example, a central processing unit (CPU), a micro processing unit (MPU), or a digital signal processor (DSP). At least some functions implemented by the processor 101 executing a program may be implemented by an electronic circuit such as an application specific integrated circuit (ASIC) or a programmable logic device (PLD).

The memory 102 is used as a main storage device of the computer 100. The memory 102 temporarily stores at least a part of an operating system (OS) program and an application program to be executed by the processor 101. In addition, the memory 102 stores various types of data to be used in processing by the processor 101. As the memory 102, for example, a volatile semiconductor storage device such as a random access memory (RAM) is used.

The peripheral devices coupled to the bus 109 include a storage device 103, a graphic processing device 104, an input interface 105, an optical drive device 106, a device coupling interface 107, and a network interface 108.

The storage device 103 electrically or magnetically performs data writing and reading on a built-in recording medium. The storage device 103 is used as an auxiliary storage device of the computer. The storage device 103 stores OS programs, application programs, and various types of data. Note that, as the storage device 103, for example, a hard disk drive (HDD) or a solid state drive (SSD) can be used.

A monitor 21 is coupled to the graphic processing device 104. The graphic processing device 104 displays an image on a screen of the monitor 21 in accordance with an instruction from the processor 101. Examples of the monitor 21 include a display device using organic electro luminescence (EL) and a liquid crystal display device.

A keyboard 22 and a mouse 23 are coupled to the input interface 105. The input interface 105 transmits signals sent from the keyboard 22 and the mouse 23 to the processor 101. Note that the mouse 23 is an example of a pointing device, and another pointing device can also be used. Examples of the another pointing device include a touch panel, a tablet, a touch pad, and a track ball.

The optical drive device 106 uses laser light or the like to read data recorded in an optical disc 24 or write data to the optical disc 24. The optical disc 24 is a portable recording medium in which data is recorded so as to be readable by reflection of light. Examples of the optical disc 24 include a digital versatile disc (DVD), a DVD-RAM, a compact disc read only memory (CD-ROM), and a CD-recordable (R)/rewritable (RW).

The device coupling interface 107 is a communication interface for coupling the peripheral devices to the computer 100. For example, a memory device 25 and a memory reader/writer 26 can be coupled to the device coupling interface 107. The memory device 25 is a recording medium equipped with a communication function with the device coupling interface 107. The memory reader/writer 26 is a device that writes data to a memory card 27 or reads data from the memory card 27. The memory card 27 is a card-type recording medium.

The network interface 108 is coupled to a network 20. The network interface 108 transmits and receives data to and from another computer or a communication device via the network 20. The network interface 108 is a wired communication interface coupled to a wired communication device such as a switch or a router with a cable, for example. In addition, the network interface 108 may be a wireless communication interface that is coupled to and communicates with a wireless communication device such as a base station or an access point with radio waves.

The computer 100 can implement the processing function of the second embodiment with hardware—as described above. Note that the quantum chemical computing device 10 illustrated in the first embodiment also can be implemented by hardware similar to the hardware of the computer 100 illustrated in FIG. 2.

The computer 100 implements the processing function of the second embodiment by executing, for example, a program recorded in a computer-readable recording medium. The program in which the processing contents to be executed by the computer 100 are described can be recorded in a variety of recording media. For example, the program to be executed by the computer 100 may be stored in the storage device 103. The processor 101 loads at least a part of the program in the storage device 103 into the memory 102 and executes the program. It is also possible to record the program to be executed by the computer 100 in a portable recording medium such as the optical disc 24, the memory device 25, or the memory card 27. The program stored in the portable recording medium can be executed after being installed in the storage device 103 under the control of the processor 101, for example. In addition, the processor 101 also can read the program directly from the portable recording medium and execute the program.

The computer 100 solves the Schrödinger equation for a predetermined molecule by the Hartree-Fock computation or computations incorporating electron correlation. When the molecule to be analyzed is in a stable state, the computer 100 can often obtain the ground state that minimizes the energy, by placing the electrons in order from the molecular orbital having the lowest energy level. However, when the electron configuration that minimizes the energy in a deformed state of the molecule is to be found, the accuracy of computation deteriorates unless computations incorporating electron correlation are performed.

Figure 3:
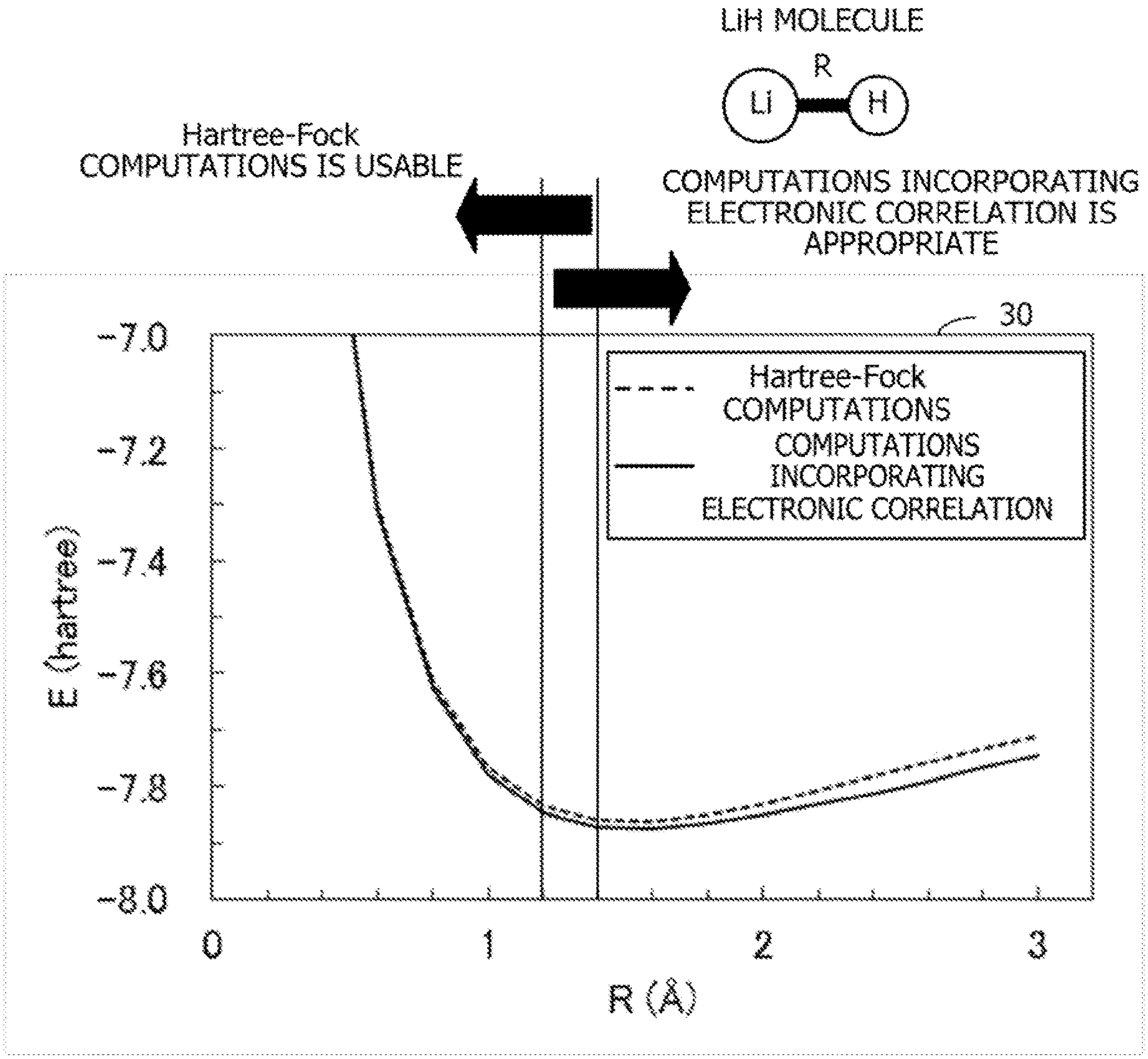
FIG. 3 is a diagram illustrating an example of computation of energy according to the state of a molecule.

FIG. 3 is a diagram illustrating an example of computation of energy according to the state of a molecule. In FIG. 3, the graph 30 illustrates an example of computing the value of energy according to an interatomic distance R for an LiH molecule. In the graph 30, the horizontal axis denotes the interatomic distance R (Å), and the vertical axis denotes the energy (hartree). The dashed line in the graph 30 indicates the energy value found by the Hartree-Fock computations, and the solid line indicates the energy value found by computations incorporating electron correlation.

As long as the interatomic distance R is short, there is almost no difference in energy values between the Hartree-Fock computations and the computations incorporating electron correlation. As the distance R becomes longer, the difference in energy values between the Hartree-Fock computations and the computations incorporating electron correlation increases. Note that it is known that the computations incorporating electron correlation are more highly accurate computations. Therefore, as long as the distance R is shorter than a certain level, the Hartree-Fock computations may be usable if the computation accuracy is acceptable. However, when the distance R becomes equal to or longer than a certain level and the computation accuracy of the Hartree-Fock computations becomes worse to an unacceptable extent, it is appropriate to perform computations incorporating electronic correlation (CI computations).

For example, in the case of the LiH molecule illustrated in FIG. 3, computations incorporating the electron correlation are appropriate in the area of the distance R equal to or longer than R=1.2 to 1.4 Å where the effect of electron correlation becomes larger. Here, when the scale of the system is small and the number of basis functions is small, such as the LiH molecule, the number of molecular orbitals (the number of basis functions) is also small, and accordingly, the full-CI computations taking all possible electron configurations into consideration are also practicable. However, as the scale of the system increases and the number of molecular orbitals also increases, the full-CI computations become difficult.

Thus, the computer 100 will include some molecular orbitals among all molecular orbitals into the active space orbital group and perform the CI computations with the possible electron configurations limited to the active space orbital group. At this time, it is important to appropriately select the molecular orbitals to be included into the active space orbital group in order to perform accurate computations incorporating more effects of electron correlation while suppressing the computational load.

Note that quantum chemical computations also can be performed using a quantum computer. When quantum chemical computations are performed using a quantum computer, the number of quantum bits used for computations increases as the number of molecular orbitals to which electrons are placed increases. In order for quantum computers having physical limitations on the number of quantum bits that can be used (particularly NISQs: noisy intermediate-scale quantum computers) to perform quantum chemical computations efficiently, there is no option but to limit the number of molecular orbitals where electrons can be placed. Therefore, it is very important to appropriately select molecular orbitals to be included in the active space orbital group also in quantum chemical computations using a quantum computer.

Traditionally, the active space orbital group is selected from among a plurality of molecular orbitals near the highest occupied molecular orbital (HOMO) and the lowest unoccupied molecular orbital (LUMO) among the molecular orbitals obtained by the Hartree-Fock method. Then, quantum chemical computations are performed taking into consideration the electron configurations formed from the active space orbital group including the selected molecular orbitals.

However, even if selection is made from among molecular orbitals near HOMO and LUMO, not all obtained active space orbital groups are optimal. Therefore, experience and intuition are often expected in selecting the active space orbital group. In order to determine the optimal active space orbital group, quantum chemical computations will be performed for a plurality of active space orbital groups, and it will be confirmed which active space orbital group is used when the energy further lowers. Performing quantum chemical computations for a plurality of active space orbital groups in this manner involves a large cost of computation.

Here, attention is focused on the magnitude of interaction between molecular orbitals as a selection criterion for appropriately selecting molecular orbitals to be included in the active space orbital group. The magnitude of interaction between molecular orbitals has connection with the magnitude of overlap integral between molecular orbitals. By including molecular orbitals with larger overlap integrals into the active space orbital group, a set of molecular orbitals having strong interaction is included into the active space orbital group, and there is a possibility that the energy can be further lowered with the influence of the interaction.

The reason why it is appropriate to include molecular orbitals with large overlap integrals into the active space orbital group will be qualitatively explained below.

The CI method is used to describe complex electronic states (states incorporating electron correlation) that are not representable by only one certain electron configuration (such as the Hartree-Fock electron configuration). When electron correlation is incorporated in the CI method, more diverse electronic states are expressed by mixing a plurality of electron configurations. In order to incorporate more electron correlation, it is advantageous to have stronger interaction between molecular orbitals (that is, larger exchange of electrons between orbitals) included in the electron configuration to be taken into consideration. The magnitude of the interaction between molecular orbitals is closely related to the magnitude of the overlap integral between these orbitals, and the interaction between the orbitals becomes stronger due to larger overlap integral. Therefore, by including molecular orbitals with large overlap integrals with other molecular orbitals into the active space orbital group and ensuring that electrons can be placed in those molecular orbitals, the possibility of creating such an electronic state that lessens the total energy increases.

Figure 4:
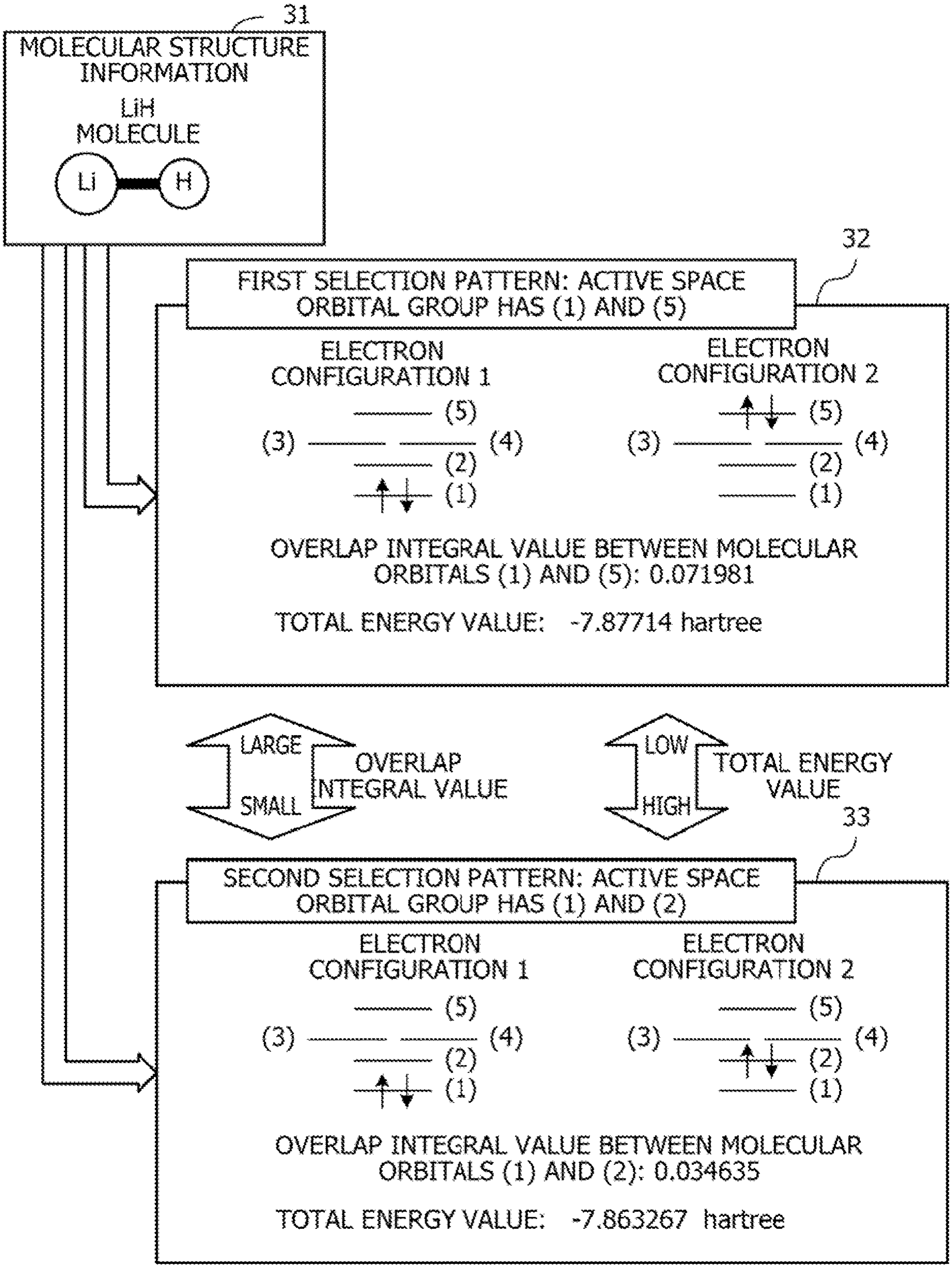
FIG. 4 is a diagram illustrating a first example of the relationship between an overlap integral value between molecular orbitals included in the active space orbital group and the total energy value.

FIG. 4 is a diagram illustrating a first example of the relationship between the overlap integral value between molecular orbitals included in the active space orbital group and the total energy value. In the example in FIG. 4, a case where the quantum chemical computations are performed based on molecular structure information 31 indicating the LiH molecule is supposed. Five molecular orbitals are obtained by finding the molecular orbitals of the LiH molecule by the Hartree-Fock method. In FIG. 4, each molecular orbital is represented by the horizontal line. The respective molecular orbitals are assigned with the numbers (1) to (5) indicating the order from the lowest energy level. As examples of the selection pattern for molecular orbitals to be included in the active space orbital group, a first selection pattern 32 that selects the molecular orbitals (1) and (5), and a second selection pattern 33 that selects the molecular orbitals (1) and (2) are illustrated.

In the first selection pattern 32, an electron configuration in which two electrons are placed in the molecular orbital (1) and an electron configuration in which two electrons are placed in the molecular orbital (5) are conceivable. In addition, the overlap integral value between the molecular orbitals (1) and (5) selected in the first selection pattern 32 is "0.071981". Then, the total energy value obtained by the active space orbital group of the first selection pattern 32 is "−7.87714 (hartree)".

The wave function of the molecule subject to the quantum chemical computations is represented by a linear combination of configuration state functions (CSFs) representing respective electron configurations. By solving the Schrödinger equation for that wave function, the total energy value is obtained.

In the second selection pattern 33, an electron configuration in which two electrons are placed in the molecular orbital (1) and an electron configuration in which two electrons are placed in the molecular orbital (2) are conceivable. In addition, the overlap integral value between the molecular orbitals (1) and (2) selected in the second selection pattern 33 is "0.034635". Then, the total energy value obtained by the active space orbital group of the second selection pattern 33 is "−7.863267 (hartree)".

In the example illustrated in FIG. 4, the first selection pattern 32 whose active space orbital group is made up of the molecular orbitals (1) and (5) has a larger overlap integral value than the second selection pattern 33 whose active space orbital group is made up of the molecular orbitals (1) and (2). Then, the first selection pattern 32 having a larger overlap integral value has a lower total energy value than the second selection pattern 33 having a smaller overlap integral value.

Figure 5:
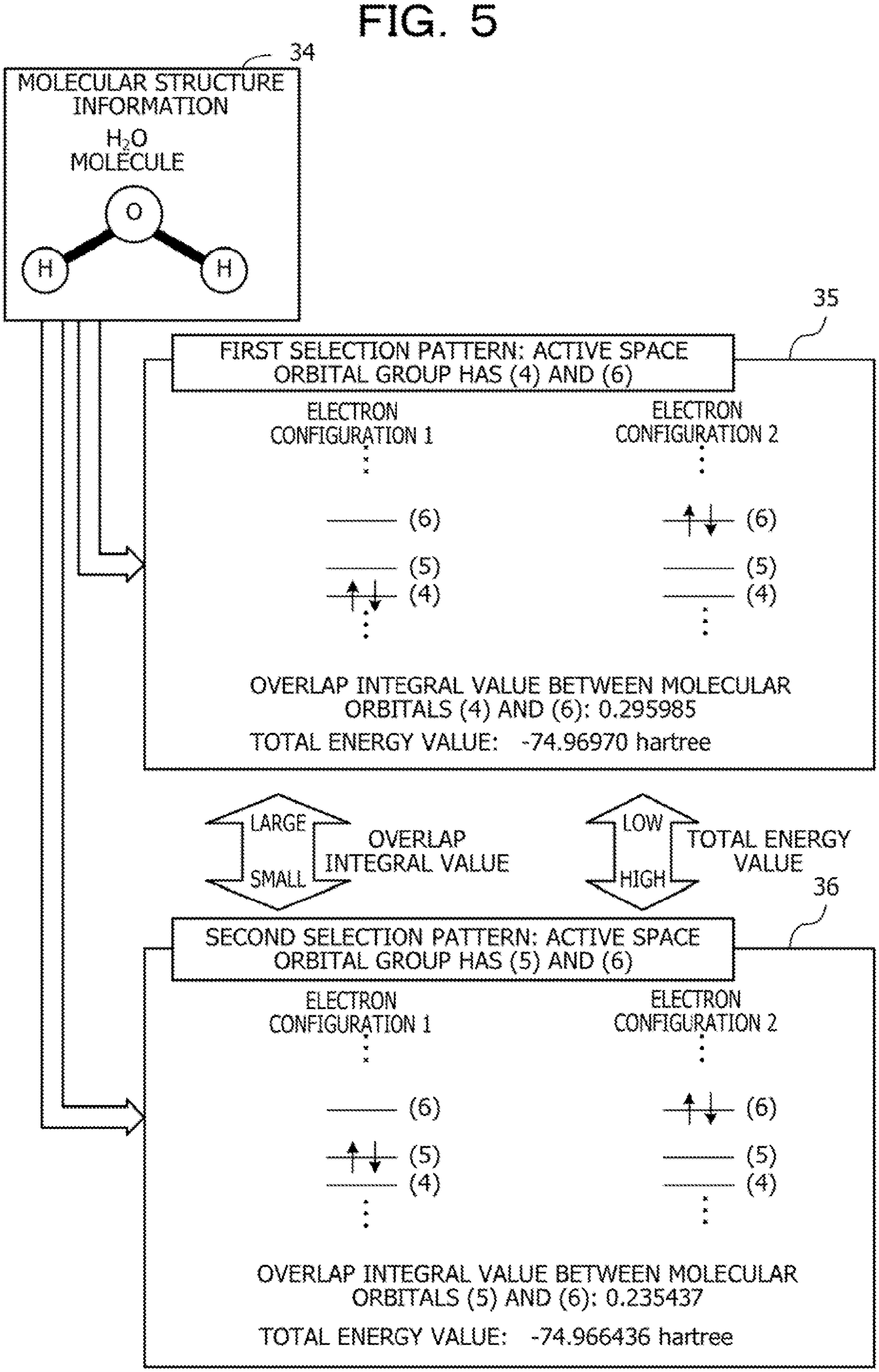
FIG. 5 is a diagram illustrating a second example of the relationship between the overlap integral value between molecular orbitals included in the active space orbital group and the total energy value.

FIG. 5 is a diagram illustrating a second example of the relationship between the overlap integral value between molecular orbitals included in the active space orbital group and the total energy value. In the example in FIG. 5, a case where the quantum chemical computations are performed based on molecular structure information 34 indicating the $H_2O$ molecule is supposed. A large number of molecular orbitals are obtained by finding the molecular orbitals of the $H_2O$ molecule by the Hartree-Fock method. In FIG. 5, each of the fourth to sixth molecular orbitals from the lowest energy level is indicated by the horizontal line. The respective molecular orbitals are assigned with the numbers (4) to (6) indicating the order from the lowest energy level. As examples of the selection pattern for molecular orbitals to be included in the active space orbital group, a first selection pattern 35 that selects the molecular orbitals (4) and (6), and a second selection pattern 36 that selects the molecular orbitals (5) and (6) are illustrated.

In the first selection pattern 35, an electron configuration in which two electrons are placed in the molecular orbital (4) and an electron configuration in which two electrons are placed in the molecular orbital (6) are conceivable. In addition, the overlap integral value between the molecular orbitals (4) and (6) selected in the first selection pattern 35 is "0.295985". Then, the total energy value obtained by the active space orbital group of the first selection pattern 35 is "−74.96970 (hartree)".

In the second selection pattern 36, an electron configuration in which two electrons are placed in the molecular orbital (5) and an electron configuration in which two electrons are placed in the molecular orbital (6) are conceivable. In addition, the overlap integral value between the molecular orbitals (5) and (6) selected in the second selection pattern 36 is "0.235437". Then, the total energy value obtained by the active space orbital group of the second selection pattern 36 is "−74.966436 (hartree)".

In the example illustrated in FIG. 5, the first selection pattern 35 whose active space orbital group is made up of the molecular orbitals (4) and (6) has a larger overlap integral value than the second selection pattern 36 whose active space orbital group is made up of the molecular orbitals (5) and (6). Then, the first selection pattern 35 having a larger overlap integral value has a lower total energy value than the second selection pattern 36 having a smaller overlap integral value.

As illustrated in FIGS. 4 and 5, a lower total energy value can be obtained when a molecular orbital having a larger overlap integral value with other molecular orbitals is included in the active space orbital group. Thus, when selecting the active space orbital group in quantum chemical computations, the computer 100 is assumed to preferentially include a molecular orbital having a larger overlap integral value with other molecular orbitals into the active space orbital group.

Figure 6:
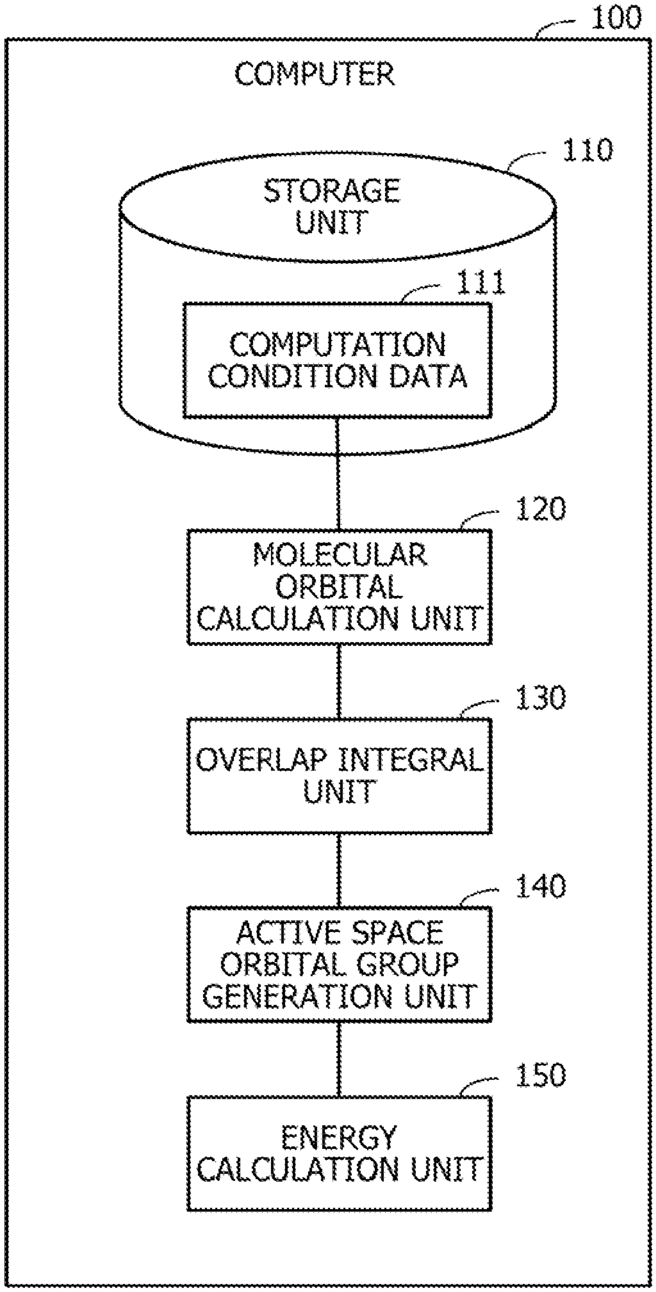
FIG. 6 is a block diagram illustrating an example of functions for quantum chemical computations by the computer.

FIG. 6 is a block diagram illustrating an example of functions for quantum chemical computations by the computer. The computer 100 includes a storage unit 110, a molecular orbital calculation unit 120, an overlap integral unit 130, an active space orbital group generation unit 140, and an energy calculation unit 150.

The storage unit 110 stores molecular structure information indicating the structure of a molecule subject to quantum chemical computations and computation condition data 111 including conditions for quantum chemical computations of that molecule. For example, a part of the storage area of the memory 102 or the storage device 103 is used as the storage unit 110.

The molecular orbital calculation unit 120 calculates molecular orbitals of the molecule subject to quantum chemical computations, based on the computation condition data 111. For example, the molecular orbital calculation unit 120 calculates molecular orbitals by the Hartree-Fock method.

The overlap integral unit 130 calculates the overlap integral value between molecular orbitals. For example, the overlap integral unit 130 computes the energy level of each of a plurality of molecular orbitals. The overlap integral unit 130 assumes molecular orbitals whose energy levels are equal to or higher than a predetermined lower limit value but equal to or lower than a predetermined upper limit value, as selection candidates. The overlap integral unit 130 generates combinations between two molecular orbitals among the selection candidates and computes the overlap integral values for each combination.

The active space orbital group generation unit 140 selects molecular orbitals in order from the molecular orbital having the largest overlap integral value with other molecular orbitals and includes the selected molecular orbitals into the active space orbital group. When the number of molecular orbitals included in the active space orbital group reaches a predetermined number, the active space orbital group generation unit 140 ends the selection of molecular orbitals to be included in the active space orbital group.

The energy calculation unit 150 calculates the total energy value of the molecule subject to quantum chemical computations, based on the generated active space orbital group. The energy calculation unit 150 outputs the calculated total energy value as the result of quantum chemical computations. For example, the energy calculation unit 150 stores the calculated total energy value in the memory 102 or the storage device 103. In addition, the energy calculation unit 150 may display the calculated total energy value on the monitor 21.

Note that the function of each element illustrated in FIG. 6 can be implemented by, for example, causing the computer to execute a program module corresponding to each element. In addition, the computation condition data 111 for performing quantum chemical computations is input in advance to the computer 100 by a user and stored in the storage unit 110.

FIG. 7 is a diagram illustrating an example of the computation condition data. FIG. 7 illustrates the computation condition data 111 indicating the structure of the LiH molecule. The computation condition data 111 uses the STO-3G basis function. The STO-3G basis function is a minimal basis function system that fits three primitive Gaussian orbitals to a single Slater-type orbital (STO). In addition, in the computation condition data 111, a value when the Li—H interatomic distance R=1.4 Å is satisfied is set.

The meaning of each item in the computation condition data 111 is as follows. The computing method used for quantum chemical computations is indicated by "method". In the example in FIG. 7, the Hartree-Fock method is designated as the computing method. The basis function system to be applied is indicated by "basis". The charge of the entire molecule is indicated by "charge". The spin multiplicity is indicated by "spin multiplicity". The coordinates of each atom that constitutes the molecule is indicated by "geometry". The coordinates of each constituent atom specify information regarding the molecular structure, such as the interatomic distances (bond distances) and bond angles. The minimum value ($E_{min}$) of the energy level taken into consideration in the overlap integral computations is indicated by "energy level minimum". The maximum value ($E_{max}$) of the energy level taken into consideration in the overlap integral computations is indicated by "energy level maximum".

Next, a procedure for quantum chemical computations will be described.

Figure 8:
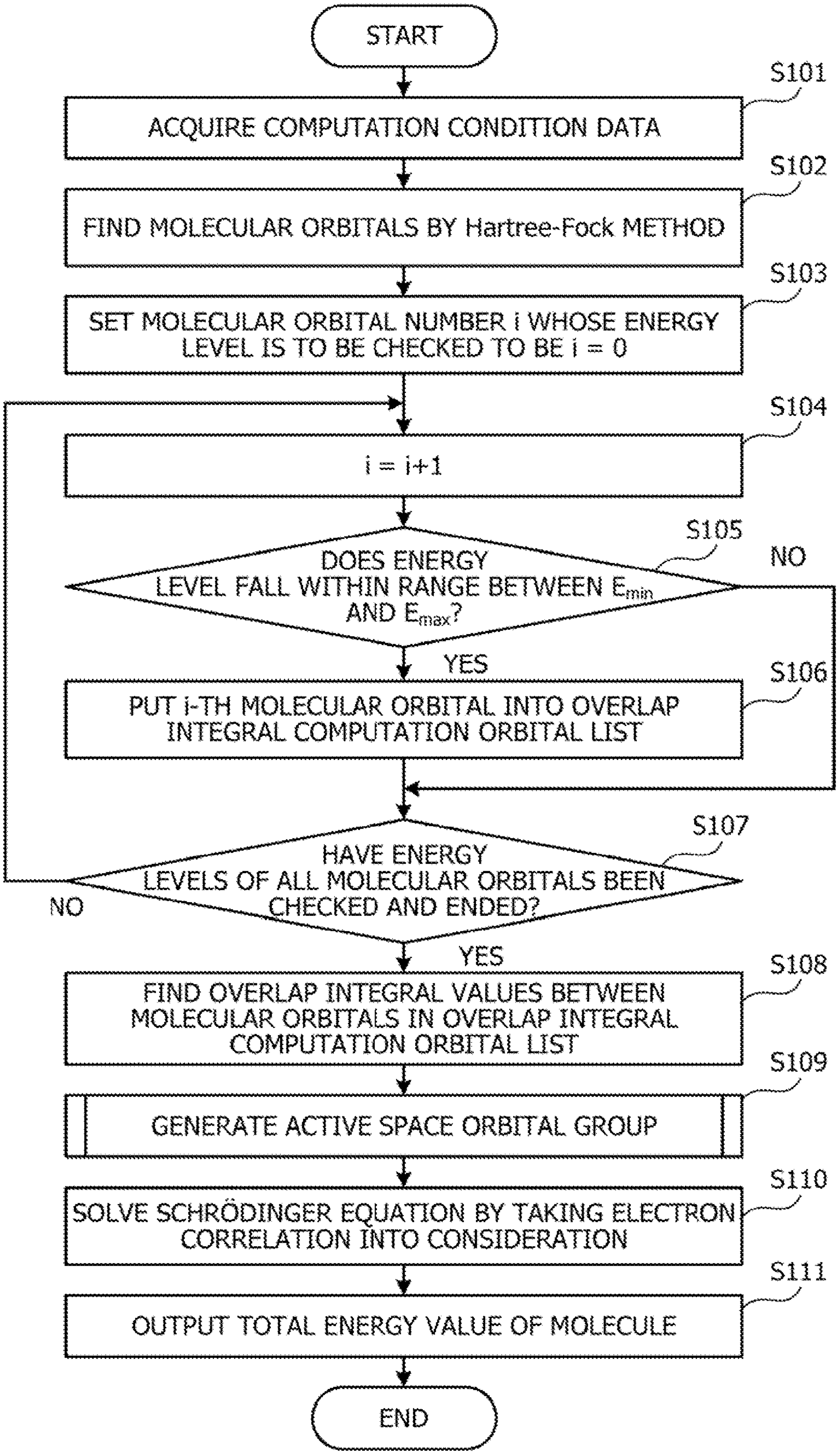
FIG. 8 is a flowchart illustrating an example of the procedure for quantum chemical computations.

FIG. 8 is a flowchart illustrating an example of the procedure for quantum chemical computations. Hereinafter, the process illustrated in FIG. 8 will be described in line with step numbers.

[Step S101] The molecular orbital calculation unit 120 acquires the computation condition data 111. For example, the molecular orbital calculation unit 120 accepts an input designating the computation condition data 111 of a molecule subject to quantum chemical computations, from a user, and reads the designated computation condition data 111 from the storage unit 110.

[Step S102] The molecular orbital calculation unit 120 finds molecular orbitals by the Hartree-Fock method. The molecular orbital calculation unit 120 assigns one or more found molecular orbitals with molecular orbital numbers in ascending order from one. The molecular orbital calculation unit 120 transmits information indicating the molecular orbitals to the overlap integral unit 130.

[Step S103] The overlap integral unit 130 sets the initial value "0" in a variable i indicating the molecular orbital number whose energy level is to be checked (i=0).

[Step S104] The overlap integral unit 130 adds one to the variable i (i=i+1).

[Step S105] The overlap integral unit 130 verifies whether or not the energy level of the i-th molecular orbital falls within the range between the minimum value ($E_{min}$) of the energy level and the maximum value ($E_{max}$) of the energy level. For example, the overlap integral unit 130 advances the process to step S106 if the energy level of the relevant molecular orbital is equal to or higher than $E_{min}$ and equal to or lower than $E_{max}$. In addition, when the energy level of this molecular orbital is lower than $E_{min}$ or higher than $E_{max}$, the overlap integral unit 130 advances the process to step S107.

[Step S106] The overlap integral unit 130 puts the i-th molecular orbital into an overlap integral computation orbital list.

[Step S107] The overlap integral unit 130 verifies whether or not the energy levels of all molecular orbitals have been checked and ended. If all molecular orbitals have been checked and ended, the overlap integral unit 130 advances the process to step S108. In addition, if there is an unchecked molecular orbital, the overlap integral unit 130 advances the process to step S104.

[Step S108] The overlap integral unit 130 finds the overlap integral values between molecular orbitals in the overlap integral computation orbital list. For example, the overlap integral unit 130 generates molecular orbital pairs of all combinations that can be generated by selecting two molecular orbitals from the overlap integral computation orbital list. The overlap integral unit 130 computes the overlap integral values separately for all the generated molecular orbital pairs. An overlap integral value $S_{ij}$ between the i-th molecular orbital and the j-th molecular orbital can be calculated by the following formula.

[Mathematical Formula 1]

$$S_{ij}=\int\psi_i^*(r)\psi_j(r)dr \quad (1)$$

In formula (1), the complex conjugate of the atomic orbital function of the i-th molecular orbital is denoted by $\psi_i^*(r)$. The atomic orbital function of the j-th molecular orbital is denoted by $\psi_j(r)$. Formula (1) takes a larger value as the overlap between the two molecular orbitals increases. When the two molecular orbitals do not overlap, the overlap integral value takes "0", and when the two molecular orbitals completely overlap, the overlap integral value takes "1".

[Step S109] The active space orbital group generation unit 140 generates the active space orbital group based on the overlap integral values for each molecular orbital pair. Details of this process will be described later (see FIG. 9).

[Step S110] The energy calculation unit 150 solves the Schrödinger equation based on the electron configurations according to the active space orbital group, by taking the electron correlation into consideration. This gives the total energy value of the molecule.

[Step S111] The energy calculation unit 150 outputs the total energy value of the molecule as a result of quantum chemical computations.

Figure 9:
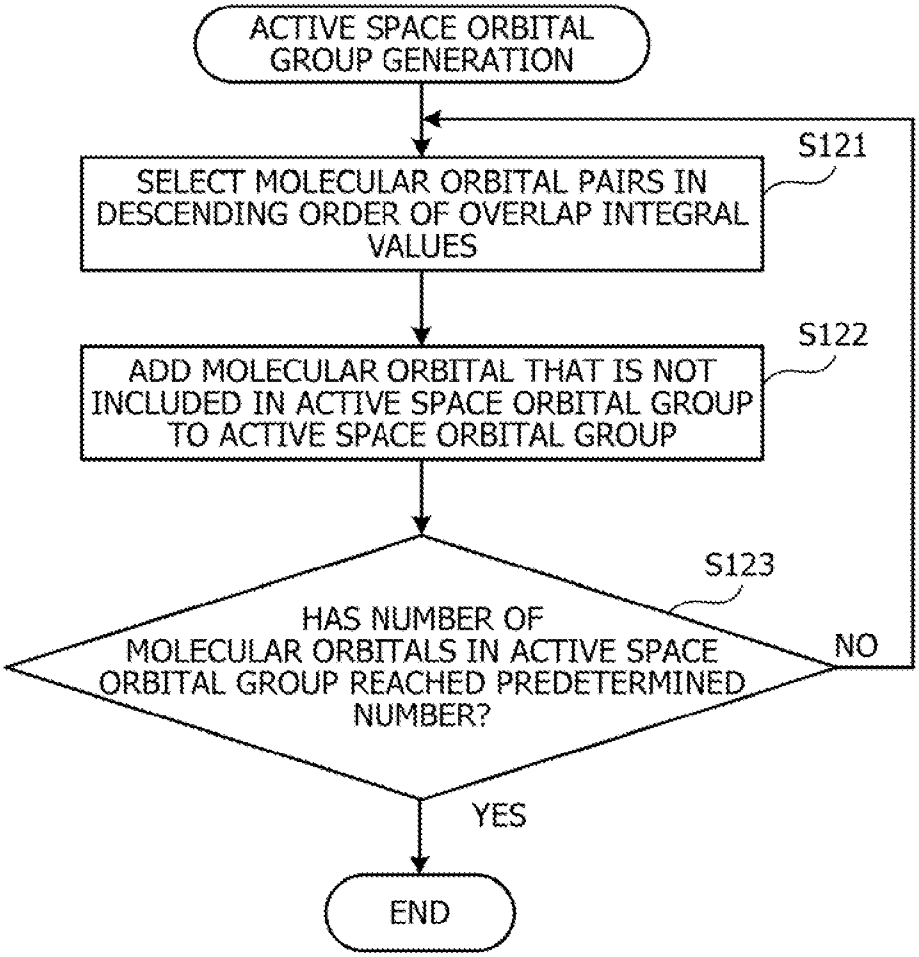
FIG. 9 is a flowchart illustrating an example of the procedure of an active space orbital group generation process.

FIG. 9 is a flowchart illustrating an example of the procedure of an active space orbital group generation process. Hereinafter, the process illustrated in FIG. 9 will be described in line with step numbers.

[Step S121] The active space orbital group generation unit 140 selects molecular orbital pairs in descending order of overlap integral values.

[Step S122] The active space orbital group generation unit 140 adds a molecular orbital that is not included in the active space orbital group among the molecular orbitals included in the selected molecular orbital pairs, to the active space orbital group.

[Step S123] The active space orbital group generation unit 140 verifies whether or not the number of molecular orbitals in the active space orbital group has reached a predetermined number. When the number of molecular orbitals has reached the predetermined number, the active space orbital group generation unit 140 ends the active space orbital group generation process. In addition, if the number of molecular orbitals is less than the predetermined number, the active space orbital group generation unit 140 advances the process to step S121.

In this manner, molecular orbitals having larger overlap integral values with other molecular orbitals are added to the active space orbital group in order.

Figure 10:
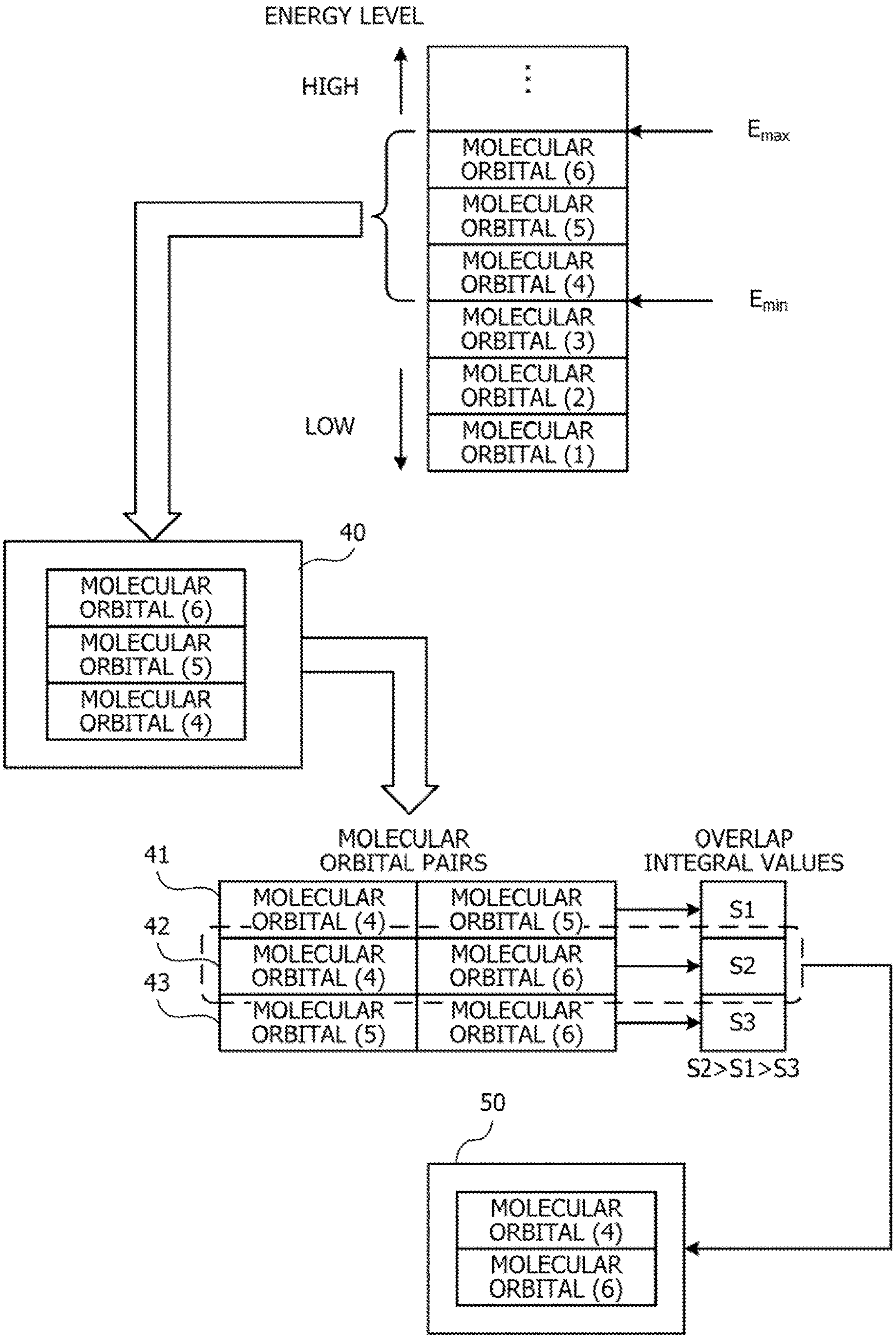
FIG. 10 is a diagram illustrating an example of generating the active space orbital group.

FIG. 10 is a diagram illustrating an example of generating the active space orbital group. When the generated molecular orbitals are arranged by energy level, the molecular orbital whose energy level is lower than the minimum value ($E_{min}$) is an orbital in which electrons are regularly placed. In addition, the molecular orbital whose energy level is higher than the maximum value ($E_{max}$) is an orbital in which electrons are not placed. Then, the molecular orbital whose energy level is between the minimum value ($E_{min}$) and the maximum value ($E_{max}$) is an orbital having the possibility that electrons are placed.

In the example in FIG. 10, the energy levels of the fourth to sixth molecular orbitals are located between the minimum value ($E_{min}$) and the maximum value ($E_{max}$). In this case, an overlap integral computation orbital list 40 including the fourth to sixth molecular orbitals is generated. Then, three molecular orbital pairs 41 to 43 are generated from molecular orbitals included in the overlap integral computation orbital list 40.

The overlap integral values are computed for each of the molecular orbital pairs 41 to 43. In the example in FIG. 10, the overlap integral value of the molecular orbital pair 41 is S1, the overlap integral value of the molecular orbital pair 42 is S2, and the overlap integral value of the molecular orbital pair 43 is S3. Here, the magnitude relationship of the overlap integral values is assumed to be "S2>S1>S3". In this case, first, the fourth molecular orbital and the sixth molecular orbital included in the molecular orbital pair 42 are included into an active space orbital group 50.

If the number of molecular orbitals to be included in the active space orbital group 50 is "2", a plurality of electron configurations is determined based on the active space orbital group 50 including two molecular orbitals. For example, it is assumed that electrons are regularly placed in molecular orbitals whose energy levels are lower than the minimum value ($E_{min}$), and electrons that are not permitted to be placed in those molecular orbitals are placed in any molecular orbital in the active space orbital group. Then, the total energy value is obtained by solving the Schrödinger equation for the wave function represented by a linear combination of the configuration state functions for each of the plurality of electron configurations.

By including molecular orbitals having large overlap integral values with other molecular orbitals into the active space orbital group 50 in this manner, highly accurate computations incorporating many effects of electron correlation may be performed more efficiently.

In other words, computations incorporating electron correlation, such as configuration interaction methods, are usually performed with the results of the Hartree-Fock computations as a starting point. The computation of the overlap integral value has to be performed only once when the Hartree-Fock computations are performed, and the computation time thereof is at an almost negligible level compared with the computation time involved in performing computations incorporating electron correlation. In the second embodiment, one active space orbital group including molecular orbitals having larger overlap integrals only has to be selected in advance and computed. In this case, the computation time is shortened to about 1/M compared with a case where, for example, M (M is an integer equal to or larger than two) active space orbital groups (for example, the respective selection patterns in FIGS. 4 and 5) are computed in a state without information regarding the overlap integral values.

In addition, molecular orbitals whose energy levels are lower than the minimum value ($E_{min}$) or higher than the maximum value ($E_{max}$) are excluded from the overlap integral computation orbital list 40 in advance. This allows a smaller number of molecular orbital pairs subject to computation of the overlap integral value and reduces the amount of computation.

OTHER EMBODIMENTS

Although the second embodiment illustrates an example in which the classical computer 100 is used to perform the entire quantum chemical computations, quantum chemical computations can also be performed using a quantum computer. For example, the process of solving the Schrödinger equation can be carried out using the quantum computer. When the quantum computer is used, a smaller number of molecular orbitals to be included in the active space orbital group 50 is allowed, and accordingly, the number of quantum bits used for computations is also made smaller. As illustrated in the second embodiment, appropriately narrowing down the number of molecular orbitals to be included in the active space orbital group 50 is a very useful technique for quantum computers (particularly NISQs) that have physical limitations on the number of quantum bits that can be used.

The above description merely indicates the principle of the present invention. Furthermore, numerous modifications and changes can be made by those skilled in the art. The present invention is not limited to the exact configuration and application examples illustrated and described above, and all corresponding modifications and equivalents are regarded within the scope of the present invention by appended claims and equivalents thereof.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A non-transitory computer-readable storage medium storing a quantum chemical computing program that causes at least one computer to execute a process, the process comprising:

generating a plurality of molecular orbital pairs that indicates a plurality of patterns of combination of two molecular orbitals, based on a plurality of molecular orbitals for a molecule subject to quantum chemical computations;

computing, for each of the plurality of molecular orbital pairs, an overlap integral value between included molecular orbitals;

ranking the plurality of molecular orbital pairs in descending order of their computed overlap integral values;

iteratively constructing an active space orbital group to comprise a predetermined number of first molecular orbitals by repeatedly selecting a molecular orbital pair from the ranked molecular orbital pairs, in order, starting from a pair having a largest overlap integral value and including, in the active space orbital group, any molecular orbital from the selected molecular orbital pair that is not already present in the active space orbital group; and terminating the iterative constructing upon the active space orbital group comprising the predetermined number of the first molecular orbitals.

2. The non-transitory computer-readable storage medium according to claim 1, wherein the generating includes generating the plurality of molecular orbital pairs by combining, from among the plurality of molecular orbitals, second molecular orbitals that have first energy levels, the first energy levels being equal to or higher than a first threshold value, the first energy levels being equal to or lower than a second threshold value larger than the first threshold value.

3. The non-transitory computer-readable storage medium according to claim 1, wherein the process further comprising computing energy of the molecule, based on electron configurations according to the first molecular orbitals included in the active space orbital group.

4. A quantum chemical computing method for a computer to execute a process comprising:

generating a plurality of molecular orbital pairs that indicates a plurality of patterns of combination of two molecular orbitals, based on a plurality of molecular orbitals for a molecule subject to quantum chemical computations;

computing, for each of the plurality of molecular orbital pairs, an overlap integral value between included molecular orbitals;

ranking the plurality of molecular orbital pairs in descending order of their computed overlap integral values;

iteratively constructing an active space orbital group to comprise a predetermined number of first molecular orbitals by repeatedly selecting a molecular orbital pair from the ranked molecular orbital pairs, in order, starting from a pair having a largest overlap integral value and including, in the active space orbital group, any molecular orbital from the selected molecular orbital pair that is not already present in the active space orbital group; and terminating the iterative constructing upon the active space orbital group comprising the predetermined number of the first molecular orbitals.

5. The quantum chemical computing method according to claim 4, wherein the determining includes determining a certain number of molecular orbitals in order from the molecular orbitals that have a largest overlap integral value, as the first molecular orbitals.

6. The quantum chemical computing method according to claim 4, wherein the generating includes generating the plurality of molecular orbital pairs by combining, from among the plurality of molecular orbitals, second molecular orbitals that have first energy levels, the first energy levels being equal to or higher than a first threshold value, the first energy levels being equal to or lower than a second threshold value larger than the first threshold value.

7. The quantum chemical computing method according to claim 4, wherein the process further comprising computing energy of the molecule, based on electron configurations according to the first molecular orbitals included in the active space orbital group.

8. A quantum chemical computing device comprising:

one or more memories; and one or more processors coupled to the one or more memories and the one or more processors configured to:

generate a plurality of molecular orbital pairs that indicates a plurality of patterns of combination of two molecular orbitals, based on a plurality of molecular orbitals for a molecule subject to quantum chemical computations, compute, for each of the plurality of molecular orbital pairs, an overlap integral value between included molecular orbitals, rank the plurality of molecular orbital pairs in descending order of their computed overlap integral values;

iteratively construct an active space orbital group to comprise a predetermined number of first molecular orbitals by repeatedly selecting a molecular orbital pair from the ranked molecular orbital pairs, in order, starting from a pair having a largest overlap integral value and including, in the active space orbital group, any molecular orbital from the selected molecular orbital pair that is not already present in the active space orbital group; and terminate the iterative constructing upon the active space orbital group comprising the predetermined number of the first molecular orbitals.

9. The quantum chemical computing device according to claim 8, wherein the one or more processors are further configured to generate the plurality of molecular orbital pairs by combining, from among the plurality of molecular orbitals, second molecular orbitals that have first energy levels, the first energy levels being equal to or higher than a first threshold value, the first energy levels being equal to or lower than a second threshold value larger than the first threshold value.

10. The quantum chemical computing device according to claim 8, wherein the one or more processors are further configured to computing energy of the molecule, based on electron configurations according to the first molecular orbitals included in the active space orbital group.

* * * * *